United States Patent [19]
Galli et al.

[11] Patent Number: 5,739,119
[45] Date of Patent: Apr. 14, 1998

[54] ANTISENSE OLIGONUCLEOTIDES SPECIFIC FOR THE MUSCARINIC TYPE 2 ACETYLCHOLINE RECEPTOR MRNA

[76] Inventors: Rachel L. Galli, 801 S. Pennsylvania Ave., Mt. Vernon, Ohio 43050; Harris R. Lieberman, 21 Canoe River Rd., Sharon, Mass. 02067; Richard E. Fine, 113 Jordan Rd., Brookline, Mass. 02146

[21] Appl. No.: 749,589

[22] Filed: Nov. 15, 1996

[51] Int. Cl.[6] .................... A61K 48/00; C12Q 1/68
[52] U.S. Cl. .................... 514/44; 435/6; 435/91.1; 435/172.3; 435/320.1; 435/325; 435/353; 536/23.1; 536/24.31; 536/24.5
[58] Field of Search .................... 435/6, 91.1, 172.3, 435/320, 325, 353; 536/23.1, 23.31, 24.5; 514/44

[56] References Cited

PUBLICATIONS

Gewirtz et al. PNAS 93:3161–3163 (1996).
Rojanasakul Adv. Drug Delivery Rev. 18(1996) 115–131.

*Primary Examiner*—John L. LeGuyader
*Attorney, Agent, or Firm*—John F. Moran; Sana A. Pratt

[57] ABSTRACT

Antisense oligonucleotides specific for the muscarinic type 2 acetylcholine receptor mRNA have been identified. Administration of these oligonucleotides to animals resulted in an increase in memory and learning. Methods for discovering other oligonucleotides with the same activity are taught, as are uses of the antisense molecules for treatment of human and animal diseases.

19 Claims, No Drawings

ANTISENSE OLIGONUCLEOTIDES SPECIFIC FOR THE MUSCARINIC TYPE 2 ACETYLCHOLINE RECEPTOR MRNA

INTRODUCTION

The cholinergic system is comprised of nervous system cells, called neurons, which use the neurotransmitter chemical acetylcholine (ACh) to communicate. The cholinergic system plays an important role in many body functions, including, but not limited to, cardiovascular, neuromuscular, gastrointestinal, and cognitive functions such as thinking and remembering [Barnes, C (1988) *Trends Neurosci* 11:163–169; McCormick, D A (1989) *Trends Neurosci* 12: 215–221]. Decrements in cognitive abilities associated with normal aging and with age-related disorders such as Alzheimer's disease are associated with decreases in cholinergic neurotransmission [Bartus R et al. (1982) *Science* 217:408–417; Mash D et al. (1985) *Science* 228:1115–1117]. A number of treatments to reverse these impairments have been evaluated in attempts to increase brain acetylcholine levels [Castro, C et al. (1990) *Behavioral Neurosci* 104: 390–393; Overstreet D (1989) In: Bond N & Siddle D (Eds.) *Psychobiology: Issues and Applications*, North-Holland: Elsevier, pp. 23–33]. Such treatments have met with limited success, one problem being the high degree of similarity between the five muscarinic receptor proteins which bind acetylcholine.

Within the central nervous system, four of the muscarinic acetylcholine receptors (mAChRs) serve an excitatory function. In contrast, the muscarinic type 2 receptor (m2AChR) is located presynaptically and functions as an autoinhibitory receptor [Kilbinger, H (1984) *Trends Pharmacol.* 5: 103–104; McKinney, M et al. (1993) *J. Pharmacol. Exp. Ther.* 264:74–78]. Cholinergic neurotransmission depends in part on the binding of acetylcholine to the five subtypes of muscarinic receptors, labeled type 1 (M1) to type 5 (M5). Pharmacological characterization of the differences between subtypes has demonstrated considerable similarity in binding profiles, especially among the subtypes M1, M3 & M5 and between subtypes m2AChR a M4 [Brann, M et al. (1992) In: Levine, R (Ed.), *Proceedings: Subtypes of Muscarinic Receptors V. Life Sciences* 52:405–412]. Consequently, even Subtype-specific agonists or antagonists have non-selective effects due to the extent of binding to the other mAChRs. Reports based on the cloning of the mAChRs and analysis of their protein structure and messenger RNA (mRNA) transcripts support these pharmacological findings. There is considerable homology across the five subtypes with only relatively minor differences apparent [Gocayne, Jet al. (1987) *Proc. Natl. Acad.Sci. USA* 84:8296–8300; Peralta, E et al. (1987) *Science* 236:600–605; Bonner, T I (1989) *Trends Neurosci* 12: 148–151]. The similarity between receptor subtypes influences the effectiveness of traditional pharmacological treatments not only for Alzheimer's disease, but for any clinical condition improved by the modulation of the cholinergic system.

Specifically, muscarinic type 2 acetylcholine receptor (m2AChR) are important not only in brain activities, but in recovery from traumatic brain injury, and in the functioning of smooth muscle, cardiovascular, endotracheal, gastrointestinal, neuromuscular and other systems. Studies suggest that modulating m2AChR activity preferentially may upregulate cholinergic neurotransmission. In animal studies, m2AChR-selective antagonists increased extracellular ACh levels as measured by in vivo microdialysis [Quirion et al., supra; Stillman, M et al. (1991a) *Cur Separations* 10:95; Stillman, M et al. (1991b) *Soc Neurosci Abs* 17:1298; Stillman,M et al. (1993) *Brain Res* 32:385–389]. Behavioral measures of spatial learning improved following treatment with m2AChR antagonists in two studies [Packard, M et al. (1990) *Brain Res* 524:72–74; Quirion et al., supra) but not two others [Stillman, M (1994).] The effects of m2AChR antagonists and stress on hippocampal cholinergic transmission and radial arm maze performance in the rat, Dissertation, Boston University Graduate School; Messer et al. (1987) *Brain Research* 407:37–45]. All documents cited herein supra and infra are hereby incorporated by reference thereto.

Rather than using an antagonist, one might try to manipulate the levels of receptors. It has been demonstrated that oligonucleotide-based methodologies can be used to modulate protein synthesis [Amaratunga, A et al. (1993) *J. Biol. Chem.* 268:17427–17430; Crooke, S et al., U.S. Pat. No. 5,457,189; Riordan, M and Martin, J (1991) *Nature* 350:442–443]. These molecular biology techniques employ small sequences of antisense oligonucleotides that are designed and synthesized to interact with the mRNA of a specific gene. In the process of protein synthesis, DNA is activated to make mRNA which specifically codes for the assembly of the particular protein. Antisense oligonucleotides are single stranded segments of nucleotides homologous to the DNA strand that can be designed to bind to a specific mRNA, much in the same way two complementary base paired strands are bound together in the double helix structure of DNA [Uhlmann, E and Peyman, A (1990) *Chem. Rev.* 90:543–84]. When an antisense oligonucleotide is bound to the mRNA it decreases synthesis of the specific protein coded for by that message. The term antisense comes from the convention that the nucleotide sequence of the native mRNA is the "sense" sequence. An oligonucleotide constructed to be complementary to a certain segment of the sense sequence is labeled antisense and is capable of hybridizing to its homologous sense strand. In experimental applications, sense oligonucleotides are synthesized and used as negative controls. The sense oligonucleotides should be unable to bind to the mRNA of identical sequence and therefore should have no effect on gene expression. As a more stringent control, a "mismatch" oligonucleotide sequence may be used. The mismatch differs from the antisense oligonucleotide sequence in about 2–4 nucleotides. Theoretically, an antisense sequence of greater than 15 nucleotides should have only one perfectly matched target in the entire genome [Wahlestedt, C (1994) *Trends Phar.* 15:42–46]. However, if it should be the case that the antisense oligonucleotide is interacting with any gene other than its target, in theory, the mismatch is considered a better control condition than the sense sequence.

It is believed that the present invention is the first disclosure of a successful development of a m2AChR-specific antisense oligonucleotide which is capable of decreasing m2AChR binding in vitro and effecting changes in learning and memory in animals. Holopainen and Wojicik [1993, *J. Pharm. Exp Ther.* 264:423–430] developed an antisense oligonucleotide effective in decreasing receptor number for a group of G-protein coupled receptors, including muscarinic receptor subtypes. The antisense, called 7TMR, targets the area of the mRNA coding for the seventh transmembrane region (nucleotides 195–209) of the 10 proteins. This area of the gene is conserved within the group of G-protein coupled receptors which includes m2AChRs. While this antisense oligonucleotide was effective at decreasing m2AChR sites in cultured cells, it was not useful for selectively targeting the m2AChR as it affected a number of other important neurotransmitter receptors as well.

Therefore, there is a need for a method for specifically and preferentially decreasing m2AChRs without spill-over effects on other excitatory subtypes of muscarinic receptors.

SUMMARY

The present invention satisfies this need. This invention describes antisense oligonucleotides which were designed, developed and tested, employing a molecular biology technology, to upregulate acetylcholine neurotransmission in a new way. The antisense oligonucleotides developed here not only specifically decreased the number of autoinhibitory m2AChRs without spill-over effects on the other excitatory subtypes of muscarinic receptors, but also increased cholinergic neurotransmission evidenced in an enhancement in memory and learning in the animals tested. Using the invented antisense oligonucleotides to modulate cholinergic function within any of the brain or other physiological systems in which acetylcholine receptors play a role creates a new way to specifically target physiological and/or behavioral functions in a predictable manner. The use of antagonist drugs to block m2AChRs has been shown to increase extracellular ACh levels [Lapchak, P et al. (1989) Brain Res. 496:285–294; Levy et al. (1991) Pharma. Biochem Behavior 39:781–786; Stillman et al. (1993) supra]. However, even the most m2AChR specific drugs available also block excitatory M4 receptors to a lesser degree [Kilbinger, supra; Quirion et al., supra]. Using antisense oligonucleotides to manipulate the cholinergic system overcomes this problem.

The present invention has advantages over prior art methods. To date, a number of novel m2AChR ligands have been developed to improve upon available drugs. However, none of these substances approaches the selectivity of action possible with the antisense oligonucleotides of the present invention. Furthermore, these substances do not always enhance learning and memory [Stillman, M (1994), supra; Messer et al., supra]. The antisense oligonucleotides of the present invention have the ability to specifically decrease the number of autoinhibitory m2AChR both peripherally or centrally. Decreasing the density of autoinhibitory receptors increased cholinergic neurotransmission which is important in many brain and peripheral functions and disorders. The present invention overcomes a major weakness in previous pharmacological therapies which have met with limited success due, at least in part, to characteristics of cholinergic neurons and the five documented subtypes of muscarinic acetylcholine receptors [Barnes, supra; Kilbinger, supra; Quirion et al., supra].

Therefore, it is an object of the present invention to provide antisense oligonucleotides for manipulation of autoinhibitory muscarinic type 2 acetylcholine receptor (m2AChR) expression in vitro and in vivo, for use in diagnostic assays for detecting and measuring amount of m2AChR RNA, and for use as therapeutic agents for increasing cholinergic neurotransmission in an animal.

It is another object of the present invention to provide a method for decreasing m2AChR expression. Reducing m2AChR expression increases cholinergic neurotransmission which is important in treating diseases affecting learning and memory such as Alzheimer's or age-related memory impairment.

It is a further object of the present invention to provide a method for increasing cholinergic neurotransmission by decreasing m2AChR expression, useful as a treatment for any peripheral or central nervous system disease, including those involving smooth muscles, glands, the gastrointestinal tract, the cardiovascular and/or nervous system.

It is another object of the present invention to provide a method for treating diseases associated with an increase in m2AChR, the method comprising administering an effective amount of antisense oligonucleotides of the present invention such that m2AChR is decreased. Diseases would include traumatic brain injury or airway dysfunction after respiratory vital infection, for example.

It is yet another object of the present invention to provide a method for treating diseases associated with a decrease in cholinergic neurotransmission comprising administering to a patient an effective amount of antisense oligonucleotides such that m2M2AChR is decreased. Diseases include Down Syndrome, Parkinson's disease, amyotrophic lateral sclerosis-Parkinsonism-dementia complex, progressive supranuclear palsy, to name a few.

It is another object of the present invention to provide a method for detecting the level of m2AChR RNA in a cell comprising labeling the antisense oligonucleotides of the present invention and using the labeled oligonucleotides in a hybridization assay or a polymerase chain reaction assay to detect the amount of m2AChR RNA present in a cell.

It is yet another object of the present invention to provide a therapeutic agent for treating diseases associated with an increase in m2AChR, the agent comprising the antisense oligonucleotides of the present invention in a pharmaceutically acceptable amount, in a pharmaceutically acceptable excipient.

It is further another object of the present invention to provide a method for visualizing m2AChR RNA in organs, said method comprising labeling the antisense oligonucleotides of the present invention with a detectable label useful for imaging, and administering the labeled oligonucleotides at the site where imaging of m2AChR RNA is desired, and detecting the label.

DETAILED DESCRIPTION

As was discussed above, the present invention relates to antisense oligonucleotides which preferentially affect a decrease in m2AChRs while not affecting the other four subtypes of muscarinic receptors e.g., m1, m3, m4 and m5. A preferential decrease in m2AChR is a decrease whereby the ratio of m2AChR decrease to the decrease of the other four subtypes is about two to one.

The antisense oligonucleotides of the present invention are derived from the m2AChR sequence, particularly those exemplified in Table 1, and refer to a polynucleotide sequence which is comprised of a sequence of approximately at least about 8 nucleotides, is preferably not more than about 32 nucleotides, and optimally about 18, corresponding to the antisense sequence of m2AChR. Preferably, the sequence of the region from which the polynucleotide is derived is unique to m2AChR. Whether or not a sequence is unique to m2AChR can be determined by techniques known to those of skill in the art. For example, the sequence can be compared to sequences of other acetylcholine receptors in databanks, e.g., GenBank, to determine whether it is present in genes of other muscarinic receptors of an organism or not. The correspondence or non-correspondence of the derived sequence to other sequences can also be determined by hybridization under the appropriate stringency conditions. Hybridization techniques are known in the art. See for example, *Current Protocols in Molecular Biology*, John Wiley & Sons, New York, N.Y.

The antisense oligonucleotides in Table 1 were designed to interact with mRNA sequences specific for the muscarinic type 2 acetylcholine receptor and derived from a portion of the gene coding for the amino terminal of the receptor protein (nucleotides 474–491), a region of the carboxy terminal (nucleotides 1806–1823) and a portion of the nonconserved coding region for the third cytoplasmic loop of the receptor protein. All sequences were checked against GenBank files to rule out the possibility of targetting other genes of known sense oligonucleotides may be produced by any method known to the art. While those exemplified herein were synthesized using an automated synthesizer, expressed nucleotides made by one of the expression vectors used for gene therapy, such as an adenoviral, retroviral, or plasmid vector can be designed to produce antisense RNA when introduced into the body. Use of other synthetic chemistries is possible, see for example, Ulhmann and Peyman (1990)

TABLE 1

Exemplified Oligonucleotides

| Oligonucleotide | Region of Sequence | Sequence Coordinates | 5'-Sequence-3' (grouped by codons) | Seq. ID NO: |
|---|---|---|---|---|
| M2-3 | amino terminal | 474–491 | AA CTG CCA GAA GAG AAT G | 1 |
| M2-5 | carboxy terminal | 1806–1823 | AGG TCT CTG TGT TAG CAT | 2 |
| M2-9 | nonconserved region of third cytoplasmic loop | 731–748 | CAG GCA TAT TGT TAT TGT | 3 |
| M2-5M | Mismatch oligo for M2-5 | 1806–1823 | TAG CCT CTG TGT TAG GAT | 4 | sequence. When designing other m2AChR antisense oligonucleotides, it is preferable if the sequence chosen is unique to m2AChR, has a GC content of 50% or less, and does not fold upon itself to form any double stranded DNA. The genes for rat, porcine, and human muscarinic receptors have been cloned and sequenced (Bonner, I, supra). The receptor subtypes were found to be well conserved (89–98% amino acid sequence identity) in mammalian species with most of the substitutions occuring in the amino terminal or large cytoplasmic region connecting transmembrane regions five and six (as is the case with all G protein-coupled receptors, the proteins contain seven hydrophobic segments of 20–30 amino acids which are assumed to be transmembrane domains). Using the disclosed portions of the m2AChR sequence as a basis, antisense oligomers of approximately 8 nucleotides or more can be prepared from sequences of different organisms, either by excision or synthetically, which are specific for the m2AChR and are useful for detection of amount of m2AChR in a cell, decreasing amount of m2AChR expression in a cell, and treating conditions and diseases associated with cholinergic neurotransmission.

Other variants will differ from exemplified and unexemplified exact antisense oligonucleotides by one or more, preferably not exceeding 4, mismatches with the complementary m2AChR RNA, the mismatches being characterized as either substitutions or small insertions or deletions.

It will be recognized that the antisense sequences of the present invention may be part of larger oligonucleotide molecules. In other words, the antisense molecule may be flanked at either or both ends by other sequences as long as the added sequences do not interfere with the m2AChR binding specificity of the antisense oligonucleotide. These sequences may be other m2AChR antisense molecules; thereby increasing the probability of a particular antisense 5 molecule finding its target mRNA. Alternatively, the flanking sequence might be an antisense sequence to some other mRNA which one wishes to regulate simultaneously with the m2AChR. Some flanking sequences might affect stability, for example an intramolecular guanosine octet [Ojwang et al. (1995) Antimicrob. Agents Chemother. 39: 2426–2435], cellular localization, or transport.

The present invention is not limited to any particular method of making the antisense oligonucleotides. The anti- Chemical Rev. 90: 544–584. Other methods of making these oligonucleotides will be evident to those skilled in the art.

It will also be recognized that m2AChR antisense oligonucleotides of the present invention may be chemically modified or may be bound covalently or non-covalently with other molecules to reduce their degradation or increase their stability. Examples include, but are not limited to, proteins, peptides, lipids, carbohydrates, and small organic moieties, e.g., alkyl groups that might affect stability, cellular localization, or transport. A common approach to increase the half-life of oligonucleotides is the replacement of the phophodiester backbone of oligonucleotides with phosphorothioate. Other strategies include attaching oligonucleotides to DNA-protein complexes or cationic liposomes. Receptor ligands or cell-specific antibodies can be incorporated into the complexes to direct them to particular cells. The oligonucleotide may also be at least partially double stranded, either by binding to a distinct oligonucleotide or by formation of a hairpin, either at one or both termini or internally as long as the oligonucleotide is still able to decrease m2AChR expression in a cell. Cells expressing m2AChR include, but are not limited to, heart cells, smooth muscle cells such as cells in the small and large intestine, trachea and urinary bladder, prostate, and brain cells in the basal forebrain, hippocampus, striatum, cerebellar cortex, olfactory bulb, thalmus, hypothalmus, pons, and medulla.

Though exemplified herein by single-stranded DNA molecules, it will be recognized that non-DNA backbones may be substituted. For instance, an RNA or RNA-DNA hetero-oligomer antisense molecule would be useful if one desired the antisense sequence be less stable or more tightly binding than a DNA oligonucleotide. Non-naturally occurring backbones carrying bases, and capable of base pairing to natural nucleic acids, both known and not as yet invented, may be substituted for DNA or RNA oligonucleotides; such backbones may prove more stable than DNA or RNA. Extant examples of such backbones include substituting phosphorothioate or methylene groups for phosphate in linking adjacent nucleosides. Base analogues may be substituted for the commonly found A (adenosine or deoxyadenosine), G (guanosine or deoxyguanosine), C (cytidine or deoxycytidine), T (thymidine) or U (uridine). Examples include, but are not limited to, 7-aza-G and 5-methyl-C. Such base analogues are useful for adjusting the Tm of an oligonucleotide or a segment thereof. Tm, or melting temperature, is a measure of binding between two strands of a double-stranded nucleic acid; Substitution of rT (ribothymidine) for U or dU (deoxyuridine) for T are also possible. The latter substitution will be subject to attack by uracil deglycosylase, which will be slower if the dU is at a terminus of a DNA oligonucleotide. The present invention is exemplified with different antisense oligonucleotides. It will be recognized by those in the art that having shown that the invention is operative with these oligonucleotides and in accordance with other teachings of the present invention, those of ordinary skill in the art are enabled to design and test oligonucleotides, not exemplified herein, that are also operative.

In another embodiment, the present invention relates to compounds for use in the treatment or diagnosis of disease. The compounds of the present invention are antisense oligonucleotides as described above, able to preferentially decrease the number of m2AChR in a cell. The compounds of the present invention can include one or more of the above-described antisense oligonucleotides depending on the level of m2AChR decrease required, since in theory, the effect of combining the antisense oligonucleotides would be additive. The compounds of the present invention could be used as therapeutic agents to treat or diagnose disorders such as Alzheimer's disease where cognitive symptoms are related to underlying pathology involving damage to or hypofunction of cholinergic neurons, or in instances currently requiring the use of anticholinesterases. The antisense oligonucleotides could additionally be used to treat age-related memory impairments or to improve normal memory and learning abilities through enhancing cholinergic functioning. The antisense oligonucleotides would be useful for treating conditions involving m2AChRs such as traumatic brain injury or airway dysfunction after respiratory viral infection.

The compounds of the present invention may be used to detect the level of m2AChR mRNA in a sample, said sample being a cell, cell extract, purified DNA or RNA from cells, tissue, or organ, or sections of tissues or organs, or diagnose an increase in m2AChR RNA in a cell, by detecting m2AChR RNA. The level of m2AChR RNA can be detected by extracting cellular RNA and detecting the level of m2AChR RNA using a hybridization assay, such as a northern hybridization assay wherein the antisense oligonucleotides are labeled with a detectable label, or alternatively, by in situ assay of a cell or organ or tissue section using in situ hybridization techniques known to person in the art. In addition, the compounds of the present invention can be used in a polymerase chain reaction assay as primers for the detection of m2AChR RNA in cells by methods well known in the art. The compounds of the present invention may be labeled using any of a variety of labels and method of labeling. Examples of types of labels which can be used in the present invention include, but are not limited to, enzyme labels, radioisotopic labels, non-radioactive isotopic labels, fluorescent labels, and chemiluminescent labels. Such assays may also be useful for in vitro testing of potential drugs for treating a disease involving m2AChR, such as Alzheimer's, or to monitor the effect of the drug on m2AChR expression. Cell lines useful for in vitro drug testing would be those expressing m2AChR such as NG108-15.

In another embodiment, the present invention relates to a method for treating diseases or conditions involving the function of acetylcholine neurons or where manipulation of the cholinergic system is desired. Examples of diseases include, but are not limited to, decreases or alterations in cognitive functions such as learning and memory (including in normal, age-impaired, and disease-impaired, e.g., Alzheimer's disease, situations), performance enhancement (when learning, memory and other behavioral functions are impaired due to exposure to environmental or disease-induced stressors such as hypoxia, cold or heat), neuromuscular physiology such as obstructive airway disease, neuromuscular weakness and paralysis, incontinence, impotence, and central and peripheral control of motor functions, cardiovascular function (including in normal and high stress conditions), in the treatment of any peripheral or central disease where it is desirable to increase cholinergic function or decrease the function of muscarinic type 2 acetylcholine receptors, including those involving smooth muscles, glands, the gastrointestinal tract, the cardiovascular and/or nervous system. There are changes in the cholinergic system in many disorders including, but not limited to, Down Syndrome; Parkinson's disease; amyotrophic lateral sclerosis-Parkinsonism-dementia complex; progressive supranuclear palsy; Creutzfeldt-Jakob disease; and Korsakoff's syndrome.

The method would include administering an effective amount of one or more of the compounds of the present invention, or one or more m2AChR antisense oligonucleotides, to a patient requiring such a treatment, such that the level of m2AChR is decreased. The antisense oligonucleotides can be prepared for administration by methods known in the art, which can include filtering to sterilize the solution of antisense oligonucleotides, diluting or concentrating the solution, adding a stabilizer to the solution, lyophilizing the solution to produce the oligonucleotides in dried form for ease in transportation and storage. Further, the antisense oligonucleotide treatment solution can be in the form of a mixed solution which contains the antisense oligonucleotides described above and at least one other antigen or oligonucleotide, as long as the added compound does not interfere with the effectiveness of the antisense oligonucleotide treatment and adverse reactions such as toxicity are not increased additively or syntergistically. The antisense oligonucleotide treatment solution may be stored in a sealed vial, ampule or the like. The present treatment can be administered in the form of a spray for intranasal administration, or by nose drops, inhalants, eye drops, skin patch, suppository, or a capsule, liquid suspension or elixires formulated for oral administration. In the case where the treatment is in dried form, the treatment can be dissolved or suspended in sterilized distilled water or saline before administration. Any inert carrier is preferably used, such as saline, phosphate buffered saline, or any such carrier in which the antisense oligonucleotides have suitable solubility.

Generally, the method of administration of treatment may depend on the organ or organs targetted. The compounds or treatment may be administered orally, subcutaneously, or intramuscularly or intracranially by direct injection into the eye, brain or cerebral-spinal fluid, implantation of an osmotic pump, other slow-release means such as skin patch or implanted reservoir, or the like, or utilization of a means to temporarily permeabilize the blood-brain barrier since it has been demonstrated that intracranially administered oligonucleotides are readily taken up into the cells of the brain [Loke, S et al. (1989) Proc Natl Acad Sci USA 86:3474–3478; Wahlestedt, C et al. (1993) Science 259:528–31]. Improvement of oligonucleotide uptake has been achieved with different systems of vectorization including liposomes (neutral, cationic, immunoliposome), nanoparticles, or covalent attachment of a carrier [Lefebvre C et al. (1995) *Eur Cytokine Netw* 6:7–19]. Lipid-mediated transfection has also been used to deliver antisense molecules [Wang and Martini (1996) *J Clin. Invest.* 97: 448–454].

The compounds of the present invention can be administered in a dose effective for the production of a decrease in m2AChR and resulting in an improvement of the patients disease, or amelioration of the patient's disease symptoms. The treatment may be in the form of a single dose or in multi-dose program. When providing a patient with antisense oligonucleotides, the dosage administered will vary depending upon such factors as the patient's age, weight, height, sex, general medical condition, previous medical history, etc. In general, it is desirable to provide the recipient with a dosage of the above compounds which is in the range of 1 pg/kg to 500 mg/kg (body weight of patient), although a lower or higher dosage may be administered.

Described below are examples of the present invention which are provided only for illustrative purposes, and not to limit the scope of the present invention. Other suitable modifications and adaptations of the variety of conditions and parameters normally encountered in this art which are obvious to those skilled in the art are within the spirit and scope of the present invention.

EXAMPLE 1

Overview

To determine the effect of intracranially administered antisense oligonucleotides synthesized to decrease synthesis of the m2AChR, receptor binding and performance in the Morris water maze, a measure of spatial learning and memory well known in the art [Morris, R et al. (1986) *Quart. J. Exp. Psy.* 38B:365–395; Morris, R (1984) *J. Neuro. Methods* 11:47–60] were studied.

In preliminary experiments, antisense and control oligonucleotides designed to target sequences unique to the m2AChR mRNA were tested in a cell culture model. The criterion for use in subsequent animal experiments was that antisense, but not control, sequences must decrease m2AChR binding by a minimum of 50%. Changes in receptor binding were used as an indirect measure of protein synthesis, since antibodies specific to the m2AChR are not commercially available. Animal studies employed the antisense sequences found to have the most potent effect in vitro.

The animal experiments employed a between-group design. Each group (n=6–11) received either an antisense oligonucleotide, a control (mismatch) oligonucleotide, or vehicle alone. Three antisense and two control sequences were tested. Rats were surgically implanted with a 7 day mini-osmotic pump to continuously infuse oligonucleotide or vehicle directly into the lateral ventricle of the brain. Behavioral testing took place on days 5 & 6 post implantation.

In order to measure the ability of the invented antisense oligonucleotides on an m2AChR mediated cognitive behavior, spatial learning and memory were assessed using the Morris water maze (MWM) [Morris et al., supra; Shukitt-Hale, B et al. (1993) The effects of hypoxia and pharmacologic treatments on behavioral, neurochemical, and histological measures in rats, Dissertation, Boston University Graduate School; Shukitt-Hale, B et al. (1994) *Behavioral and Neural Biology* 62:244–252; Shukitt-Hale, B et al. (1996) In: *Nutritional Needs in Cold and in High Altitude Environments*, B. Marriot, Ed. National Academy Press, Washington, D.C.]. The MWM is a widely accepted measure of hippocampal acetylcholine-based learning and memory performance. The water maze is a round black pool with a single movable black platform hidden 1.5 cm below the surface of the water. Rats use distal visual cues (features of the environment) to navigate and locate the hidden platform. Rats swim well and are motivated to escape from the water onto the platform. Performance is videotaped and computer-assisted image analysis is used to measure time and distance traveled to find the hidden platform, as well as areas searched. A learning curve, measures of short and long term memory, and indices of spatial versus non-spatial search strategies were analyzed for each subject over two days of testing [Segal, M et al. (1988) *Behavioral Brain Research* 30:215–219].

Rats typically perform well on spatial memory tasks and it is often difficult to detect beneficial effects of drugs on learning and memory [Brandeis, R et al. (1989) *Int. J. Neurosci.* 48: 29–69]. Therefore, to increase the likelihood of detecting effects of m2AChR antisense treatment, rats were tested using a scopolamine-induced amnesia paradigm. In previous studies, small doses of the muscarinic antagonist scopolamine (e.g. 0.2 mg/kg) have been used to artificially decrease acetylcholine neurotransmission and thereby impair performance on cognitive tasks. Manipulations which enhance cholinergic neurotransmission, as the antisense treatment does, reverse the induced deficit in cognitive performance [Iijima, S et al. (1993) *Psychopharmacology* 112:415–420; Quirion et al., supra; Shannon, H et al. (1990) *J. Pharmacol. Exp. Therap.* 255:1071–1077].

All experiments described were approved by in-house Scientific Review and Animal Care and Use Committees and the investigators adhered to the "Guide for the Care and Use of Laboratory Animals of the Institute of Laboratory Animal Resources," National Research Council (NIH Publication No. 86-23, revised 1985).

EXAMPLE 2

Experimental Design, Methods, and Results

The development and testing of the m2AChR directed antisense oligonucleotides was conducted in three stages. In Stage I an in vitro cell culture model was used to test the effectiveness of different oligonucleotide control and antisense sequences. Stage II established the scopolamine-induced deficits in the behavioral task. In Stage III the behavioral consequences of in vivo antisense oligonucleotide treatment were assayed.

The oligonucleotide designs were based on the rat muscarinic type 2 receptor gene sequence published by Gocayne et al., supra. Antisense 3 was derived from a portion of the gene coding for the amino terminal of the receptor protein, (nucleotides 474–491), antisense 3 had a sequence of 5'-AA CTG CCA GAA GAG AAT G-3' (SEQ ID NO:1). Antisense 5 targeted a region of the carboxy terminal (nucleotides 1806–1823) with a sequence of 5'-AGG TCT CTG TGT TAG CAT-3' (SEQ ID NO:2). Antisense 9 corresponded to a portion of the nonconserved coding region for the third cytoplasmic loop of the receptor protein (nucleotides 731–748), 5'-CAG GCA TAT TGT TAT TGT-3' (SEQ ID NO:3). All sequences were checked against GenBank files to rule out the possibility of targeting other genes of known sequence.

Oligonucleotides were custom synthesized (Midland Certified Reagent Co., Midland Tex.) and delivered in a purified powder form. Oligonucleotides for cell culture experiments were synthesized with a phosphorothioate backbone, gel filter purified, and resuspended in phosphate buffered saline (PBS). For animal studies, oligonucleotides were synthesized with native phosphodiester bonds, high performance liquid chromatography purified, and resuspended in Ringer's solution. Oligonucleotides are readily soluble in aqueous solutions.

EXAMPLE 3

Stage I Experiments: Antisense Studies with Cultured Cells

A cell culture model system was employed to determine the effectiveness of specific sequences of antisense and control oligonucleotides to suppress m2AChR synthesis. The NG108-15 cell line is a mouse neuroblastoma x rat glioma hybrid line that expresses m2AChR [Stephan, C & Sastry, B (1992) Cel. Mol. Biol. 38:601–612]. These preliminary in vitro experiments determined the most effective antisense oligonucleotide sequences prior to in vivo testing in rats.

In order to determine the effect of oligonucleotide treatment, cells cultured in 75 cm2AChR flasks were exposed to a control condition, (vehicle-alone, sense or mismatch oligonucleotide), or antisense oligonucleotides at concentrations ranging from 250 nM to 10 TM, in low serum media. After 3 to 5 days the cells were assayed for m2AChR binding using standard tests. Receptor binding was measured using the radioactively tagged ligand [$^3$H]-Quinuclidinyl benzilate, a high affinity muscarinic antagonist. Antisense oligonucleotides targeting several mRNA sequences unique to the m2AChR were evaluated for effectiveness in changing receptor binding levels.

Three antisense oligonucleotides, labeled numbers 3, 5, & 9, were tested as were sense and mismatch control sequences for antisense 3. The oligonucleotides were applied at 3 concentrations, low (250 nM), medium (5 TM), or high (10 TM) for 4.5 days. All doses were repeated at least once and results averaged, except for antisense 5 (because of a limited supply.) Several concentrations of antisense oligonucleotide decreased specific binding by 50% or more, as compared to the vehicle control. These results clearly demonstrated that the antisense oligonucleotides had biologic potency to decrease m2AChR synthesis. Outcomes are summarized in Table 2 below. Not every oligonucleotide was tested at each concentration, empty cells indicate that no data was collected for these points.

Antisense 3 treatment decreased receptor binding levels by 50% at all three concentrations. Sense and mismatch controls reduced specific binding by 10% and 28% respectively. No change was seen in binding levels with a low concentration of antisense 5, however a high concentration reduced 3H-QNB binding by 60%. Antisense 9 reduced binding by 39% at 250 nanomolar and by 52% at both the 5 and 10 micromolar concentrations.

Having successfully decreased m2AChR binding by 50% or more, the three antisense sequences were used in subsequent animal studies, along with the appropriate control sequences.

TABLE 2

Receptor binding results for antisense 3, 5 & 9 treated cells.

| Condition | LOW CONC. 250 nM | MEDIUM CONC. 5 TM | HIGH CONC. 10 TM |
|---|---|---|---|
| Antisense 3 | ⓪50% | ⓪50% | ⓪55% |
| Sense 3 | — | ⓪10% | — |
| Mismatch 3 | — | ⓪28% | — |
| Antisense 5 | no change | — | ⓪60% |
| Antisense 9 | ⓪39% | ⓪52% | ⓪52% |

Note.
Changes in receptor binding relative to control vehicle treated cells, (⓪) indicates a decrease, (—) indicates that this condition was not tested.

EXAMPLE 4

Stage II Experiments: Scopolamine-Induced Deficits in The Morris Water Maze Task To establish a suitable behavioral task, a variation of the Morris water maze (MWM) test [Morris et al., supra; Segal et al., supra] was employed. As outlined in the overview above, a testing situation was set up where enhanced cholinergic activity would be expected to result in improved learning and memory in rats. Small doses of scopolamine decrease cholinergic neurotransmission and treatments which increase acetylcholine activity improve cognitive performance. Therefore the scopolamine-induced deficit paradigm was established. Stage II experiments used naive rats administered scopolamine or saline, and determined group size, assessed the appropriateness of the behavioral measures, and troubleshot technical problems. In addition, the minimum dose of scopolamine necessary to significantly impair performance in the swim task was determined to be 0.2 mg/kg [Iijima et al., supra; Quirion et al., supra]. Finally, rats implanted with vehicle loaded pumps were tested in the final version of the MWM, with and without scopolamine, to establish control performance levels.

The water maze is a round 134 cm diameter black pool filled with room temperature water (21° C.) to a depth of 30 cm. A single movable black platform (10 cm diameter) is hidden 1.5 cm below the surface of the water. Rats use distal visual cues, features of the environment, to navigate and locate the hidden platform. Rats swim well and are motivated to escape from the water onto the platform [Morris et al., supra; Shukitt-Hale, supra]. A video camera is suspended above the pool to record animal performance. The escape latency (time to locate and escape onto the platform), distance traveled, and quadrants searched were monitored. In addition, swim speed was calculated for each trial by dividing the distance traveled to reach the platform by the escape latency.

Rats swam 12 trials on each of the two days of MWM testing, day 1 trial 10 and day 2 trial 8 were probe trials, during which the platform was removed and rats searched for it the full 60 seconds. Day 2, trials 1–7 the start location was varied while for trials 9–12 the platform was located 180° from the original location.

A learning curve for performance on day one, trials 1–9, was evaluated. Day one, trials 9 and 12, were examined individually to investigate any differences in performance levels. When the starting location changes with each trial (day two, trials 1–7) performance benefits from the use of a spatial strategy. Rats with a spatial memory deficit will be expected to have longer escape latencies during these trials.

Areas searched during probe trials (day one trial 10 and day two trial 8) also indicate the use of spatial strategies. The percent of total swim time spent in each quadrant was analyzed for the past location of the removed platform as well as the other 3 quadrants. Reliance on non-spatial strategies gives rats an initial advantage when the platform location is changed (day two, trial 9). This is because normal rats typically use a spatial strategy and search the area of the original platform location. In contrast, rats with spatial memory deficits find the new location as readily as the old [Barnes, supra; Morris et al., supra; Silva A et al. (1992) *Science* 257:206–211].

Scopolamine, at 0.2 mg/kg, significantly affected water maze performance on the day 1, trials 1–9, learning curve for distance, on day 2 probe trial 8 quadrant analysis, and trials 9–12 learning the new platform location. As expected, scopolamine, which downregulates cholinergic activity, induced impairments in learning and spatial memory.

EXAMPLE 5

Stage III Experiments: Behavioral Consequences of Antisense Treatment in Rats In order to determine the behavioral effects of antisense oligonucleotide treatment performance in the Morris water maze was analyzed comparing the antisense oligonucleotide sequences that had proved effective in Stage I experiments with vehicle-alone and mismatch oligonucleotide controls.

Rats were administered vehicle alone, antisense or mismatch oligonucleotides delivered by mini-osmotic pumps into the lateral cerebral ventricle of the brain. Continuous infusion was maintained for 6 days at a rate of 0.5 Tl/hr, oligonucleotide concentration was 6 Tg/Tl, for a daily dose of 72 Tg. On days 5 and 6 of infusion rats were tested in a 2 day version of the Morris water maze task. Cholinergic neurotransmission was artificially impaired by scopolamine in order to increase the likelihood of detecting treatment effects (Brandeis et al., supra). Therefore, groups (Antisense+Scopolamine, Mismatch+Scopolamine and Vehicle+Scopolamine) were tested using the reversal of scopolamine-induced impairments paradigm.

Each of the water maze parameters impaired by scopolamine was improved by at least one of the treatment oligonucleotides (see Tables 3 and 4, below). Even though no single antisense tested completely reversed all the scopolamine-induced deficits, for every parameter assessed evidence of efficacy (improved learning and memory) was demonstrated.

EXAMPLE 6

Mismatch 5

Surprisingly, a control oligonucleotide for antisense 5, mismatch 5, with the sequence 5'-TAG CCT CTG TGT TAG GAT-3' (SEQ ID NO:4), had a significant effect on behavior, day 1 trials 1–9. No measures of day 2 performance in the water maze were significantly affected. Theoretically, changing only one of the 18 nucleotides in the antisense sequence should prevent a "mismatched" control sequence from interacting with the antisense's target. Mismatch 5 differed by 4 nucleotides from antisense 5, and therefore was not expected to affect performance in any measure of the behavior task. One possible explanation could be that this oligonucleotide was transported into the cell more efficiently, and was therefore more available for hybridization to the mRNA, be it less stable hybridization.

Conclusions

In any case, antisense 3, 5 & 9 each target a different region of the M2 gene, and treatment with 2 of the 3 sequences improved measures of learning and spatial memory. The facts that antisense oligonucleotides decreased muscarinic receptor binding in cell culture and improved performance on the spatial learning and memory task demonstrate their ability to enhance cholinergic neurotransmission by decreasing synthesis of the targeted m2AChR autoinhibitory receptor. The invented antisense oligonucleotides would therefore be useful for research and clinical applications where physiological, behavioral or cognitive changes are related to aberrations in cholinergic neurotransmission.

TABLE 3

Morris Water Maze Performance, Distance Traveled (cm), group means ± standard deviation and significance levels of ANOVA comparisons between each group and the vehicle + scopolamine group.

| GROUP/ Analysis | VEHICLE | SALINE | AS3 | Mis3 | AS5 | Mis5 | AS9 |
|---|---|---|---|---|---|---|---|
| Day 1 Trials 1–9 | 1114 ± 240 | 699 ± 80<br>p = 0.001 | 1097 ± 248<br>p = 0.891 | 1109 ± 248<br>p = 0.971 | 907 ± 210<br>p = 0.049 | 839 ± 160<br>p = 0.017 | 919 ± 202<br>p = 0.060 |
| Day 2 Trial 9 | 380 ± 455 | 673 ± 417 | 620 ± 704 | 354 ± 408 | 650 ± 517 | 672 ± 639 | 801 ± 561 |
| Trial 12 | 258 ± 224 | 156 ± 117 | 112 ± 97 | 633 ± 633 | 136 ± 63 | 249 ± 363 | 460 ± 451 |
| Interaction Trials 9–12 | — | p = 0.180 | p = 0.016 | p = 0.072 | p = 0.057 | p = 0.357 | p = 0.147 |

Note:
Values in bold italics meet criteria for significance, p ≤0.05, two tailed.

TABLE 4

Morris Water Maze Performance, Escape Latencies (s), group means ± standard deviation and significance levels of ANOVA comparisons between each group and the vehicle + scopolamine group.

| GROUP/Analysis | VEHICLE | SALINE | AS3 | Mis3 | AS5 | Mis5 | |
|---|---|---|---|---|---|---|---|
| Day 1 | 38.6 ± 8;8 | 36.2 ± 5.8 | 38.9 ± 11.8 | 40.4 ± 10.4 | 34.0 ± 8.4 | 30.3 ± 5.3 | 32.6 ± 6.4 |
| Trials 1–9 | — | p = 0.562 | p = 0.940 | p = 0.692 | p = 0.237 | p = 0.040 | p = 0.970 |
| Day 2 | 13.8 ± 14.6 | 33.7 ± 24.7 | 23.0 ± 24.5 | 14.2 ± 18.4 | 28.8 ± 19.7 | 25.5 ± 24.6 | 31.3 ± 23 |
| Trial 9 | | | | | | | |
| Trial 12 | 8.6  7.2 | 5.7  4.7 | 5.0  3.9 | 23.4  22.9 | 6.0  3.1 | 10.1  14.6 | |
| Interaction | — | p = 0.029 | p = 0.010 | p = 0.059 | p = 0.027 | p = 0.439 | p = 0.198 |
| Trials 9–12 | | | | | | | |
| Day 2 | 30.4 ± 8.5 | 50.2 ± 4.8 | 31.2 ± 9.7 | 30.3 ± 7.0 | 37.3 ± 10.4 | 35.1 ± 7.0 | 36.8 ± 6.2 |
| Probe Trial 8[a] | — | p = 0.000 | p = 0.835 | p = 0.984 | p = 0.116 | p = 0.234 | p = 0.065 |

Notes:
[a]Percent of time spent in quadrant 2, previous location of removed platform.
Values in bold italics meet criterion for significance, $p \leq 0.05$, two tailed.

---

What is claimed is:

1. An antisense nucleic acid molecule comprising a segment complementary to a sequence unique to muscarinic type 2 receptor RNA, wherein when administered to a living organism, said antisense molecule is capable of showing a behavioral change.

2. A molecule as in claim 1, wherein said segment complementary to muscarinic type 2 acetylcholine receptor messenger RNA is an exact antisense oligonucleotide.

3. A molecule as in claim 1, wherein said segment complementary to muscarinic type 2 acetylcholine receptor is 18 nucleotides long and has no more than 4 mismatches.

4. A molecule as in claim 1, wherein said molecule comprises DNA.

5. A molecule as in claim 1, wherein said molecule comprises RNA.

6. A molecule as in claim 1, wherein said animal is a mammal.

7. A molecule as in claim 6, wherein said mammal is a human.

8. A molecule as in claim 1, said molecule being chosen from a group consisting of 5'-AA CTG CCA GAA GAG AAT G-3' (SEQ. ID. 1), 5'-AGG TCT CTG TGT TAG CAT-3' (SEQ. ID. 2), 5'-CAG GCA TAT TGT TAT TGT-3' (SEQ. ID. 3), and 5'-TAG CCT CTG TGT TAG GAT-3' (SEQ ID NO:4).

9. A method for producing a functional change in a system of an organism said change associated with expression of muscarinic type 2 receptors in cells of said organism, said method comprising introducing into said organism the molecule of claim 1, in an effective amount such that said functional change is produced.

10. The method of claim 9 wherein said system is selected from the group consisting of digestive, circulatory, respiratory, cardiovascular, peripheral nervous, central nervous, autonomic nervous, reproductive, and renal.

11. A method as in claim 9, wherein said antisense molecule is introduced by infusion into the cerebral-spinal fluid of an animal.

12. A method for increasing cholinergic neurotransmission in an animal, said method comprising administering an effective amount of the molecule of claim 1 such that a decrease in muscarinic type 2 receptor binding is effected.

13. A method for treating a disease associated with an increase in muscarinic type 2 receptors, said method comprising administering an effective amount of the molecule of claim 1 such that a decrease in type 2 receptors is effected resulting in a behavioral change.

14. A method for treating a disease associated with a decrease in learning ability, said method comprising administering an effective amount of the molecule of claim 1 such that an increase in learning ability is effected.

15. A method for treating a disease associated with a decrease in memory, said method comprising administering an effective amount of the molecule of claim 1 such that an increase in memory is effected.

16. A method for treating a disease associated with a decrease in memory according to claim 15 wherein, said disease is Alzheimer's.

17. A method for visualizing muscarinic type 2 RNA in a cell, said method comprising:

(i) labeling the molecule in claim 1 with a detectable label;

(ii) contacting said labeled molecule of (i) with RNA from said cell such that hybridization between the molecule and the RNA is effected; and (iii) visualizing label in said cell.

18. A therapeutic agent for treating diseases associated with an increase in muscarinic type 2 receptors said agent comprising the antisense oligonucleotide molecule of claim 1 in a pharmaceutically acceptable amount in a pharmaceutically acceptable excipient.

19. A composition comprising an antisense muscarinic type 2 acetylcholine receptor oligonucleotide selected from the group consisting of 5'-AA CTG CCA GAA GAG AAT G-3' (SEQ. ID. 1), 5'- AGG TCT CTG TGT TAG CAT-3' (SEQ. ID. 2), 5'- CAG GCA TAT TGT TAT TGT-3' (SEQ. ID. 3), and 5'-TAG CCT CTG TGT TAG GAT-3' (SEQ ID NO:4), which composition reduces muscarinic type 2 acetylcholine receptor binding in cells in vitro.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 18 base pairs
        ( B ) TYPE: Nucleic acid
        ( C ) STRANDEDNESS: Single
        ( D ) TOPOLOGY: Linear ( x i ) SEQUENCE DESCRIPTION: SEQ ID NO:1:

AACTGCCAGA    AGAGAATG                                              18

( 2 ) INFORMATION FOR SEQ ID NO:2:

( i ) SEQUENCE CHARACTERISTICS:
        ( A ) LENGTH: 18 base pairs
        ( B ) TYPE: Nucleic acid
        ( C ) STRANDEDNESS: Single
        ( D ) TOPOLOGY: Linear ( x i ) SEQUENCE DESCRIPTION: SEQ ID NO:2:

AGGTCTCTGT    GTTAGCAT                                              18

( 2 ) INFORMATION FOR SEQ ID NO:3:

( i ) SEQUENCE CHARACTERISTICS:
        ( A ) LENGTH: 18 base pairs
        ( B ) TYPE: Nucleic acid
        ( C ) STRANDEDNESS: Single
        ( D ) TOPOLOGY: Linear ( x i ) SEQUENCE DESCRIPTION: SEQ ID NO:3:

CAGGCATATT    GTTATTGT                                              18

( 2 ) INFORMATION FOR SEQ ID NO:4:

( i ) SEQUENCE CHARACTERISTICS:
        ( A ) LENGTH: 18 base pairs
        ( B ) TYPE: Nucleic acid

```
        ( C ) STRANDEDNESS: Single
        ( D ) TOPOLOGY: Linear ( x i ) SEQUENCE DESCRIPTION: SEQ ID NO:4:

TAGCCTCTGT    GTTAGGAT                              1 8
```